United States Patent
Iwasaki et al.

(10) Patent No.: US 8,556,799 B2
(45) Date of Patent: Oct. 15, 2013

(54) GUIDE TUBE, GUIDE TUBE APPARATUS, AND ENDOSCOPE SYSTEM

(75) Inventors: Tomokazu Iwasaki, Hachioji (JP); Eiichi Kobayashi, Tama (JP)

(73) Assignee: Olympus Corporation (JP)

( * ) Notice: Subject to any disclaimer, the term of this patent is extended or adjusted under 35 U.S.C. 154(b) by 815 days.

(21) Appl. No.: 12/637,874

(22) Filed: Dec. 15, 2009

(65) Prior Publication Data

US 2010/0152536 A1    Jun. 17, 2010

(30) Foreign Application Priority Data

Dec. 17, 2008    (JP) .................................. 2008-321481

(51) Int. Cl.
*A61B 1/00*    (2006.01)

(52) U.S. Cl.
USPC ................. 600/114; 396/17; 396/19; 348/65; 348/82; 346/107.2

(58) Field of Classification Search
USPC .................... 600/114; 396/17, 19; 346/107.2; 348/65, 82, 84–85
See application file for complete search history.

(56) References Cited

U.S. PATENT DOCUMENTS

| | | | |
|---|---|---|---|
| 5,779,623 A * | 7/1998 | Bonnell | 600/114 |
| 7,998,060 B2 * | 8/2011 | Ferren et al. | 600/114 |
| 8,092,549 B2 * | 1/2012 | Hillis et al. | 623/23.64 |
| 2004/0008853 A1 * | 1/2004 | Pelrine et al. | 381/191 |
| 2007/0015965 A1 * | 1/2007 | Cox et al. | 600/114 |
| 2007/0015966 A1 * | 1/2007 | Niwa et al. | 600/115 |
| 2007/0221233 A1 * | 9/2007 | Kawano et al. | 600/160 |
| 2007/0244354 A1 * | 10/2007 | Bayer | 600/106 |
| 2009/0012359 A1 * | 1/2009 | Tanaka et al. | 600/114 |

FOREIGN PATENT DOCUMENTS

| | | |
|---|---|---|
| JP | 04-144533 | 5/1992 |
| JP | 2002-263054 | 9/2002 |

OTHER PUBLICATIONS

Kazuya Isaki et al., Development of an Active Flexible Cable by Ciliary Vibration Drive for Scope Camera, Oct. 2006, Proceedings of the 2006 IEEE/RSJ International Conference on Intelligent Robots and Systems, pp. 3946-3951.*

Kazuya Isaki et al., "Development of an Active Flexible Cable Driven by Ciliary Vibration Mechanism," The 11th Robotics Symposia, pp. 414-419, Mar. 16, 2006.

Untranslated Office Action issued by Japanese Patent Office on Jun. 27, 2013 in connection with corresponding Japanese Patent Application No. 2008-321481.

*Development of the Vibrated Drive Type Cilia Motion Mechanism for Fiber Scope*, Niltsuma, et al., Sep. 15, 2005, 1A23, 434094; pp. 2-5.

* cited by examiner

*Primary Examiner* — Christopher Mahoney
(74) *Attorney, Agent, or Firm* — Ostrolenk Faber LLP

(57) ABSTRACT

A guide tube having a tube; a ciliary portion including many cilia inclined in a longitudinal direction of the tube, provided in an outer peripheral portion of the tube; and a vibration portion provided on the tube for vibrating the ciliary portion so as to move the tube in the longitudinal direction.

8 Claims, 10 Drawing Sheets

GUIDE TUBE, GUIDE TUBE APPARATUS, AND ENDOSCOPE SYSTEM

CROSS REFERENCE TO RELATED APPLICATION

This application claims the benefit of Japanese Application No. 2008-321481 filed in Japan on Dec. 17, 2008, the contents of which are incorporated herein by this reference.

BACKGROUND OF THE INVENTION

1. Field of the Invention

The present invention relates to a guide tube, a guide tube apparatus having the guide tube, and an endoscope system having the guide tube.

2. Description of the Related Art

An endoscope apparatus has an insertion portion, and an image pickup portion, such as a CCD, is disposed at a distal end portion of the insertion portion. A user inserts the insertion portion to a target position and observes a target with a field of view of the CCD from the distal end portion.

Here, Proceedings of the 11th Robotics Symposia (Kazuya Isaki et al., issued on Mar. 16, 2006), p. 414 to p. 419, discloses a self-propelled endoscope apparatus in which by winding a ciliary tape around an outer periphery of an endoscope insertion portion and vibrating the insertion portion by a vibration motor, the insertion portion moves in a longitudinal direction of the insertion portion.

SUMMARY OF THE INVENTION

A guide tube in an embodiment of the present invention includes a tube; a ciliary portion including many cilia inclined in a longitudinal direction of the tube, provided in an outer peripheral portion of the tube; and a vibration portion provided on the tube for vibrating the ciliary portion so as to move the tube in the longitudinal direction.

Also, a guide tube apparatus in another embodiment of the present invention includes a guide tube having a tube, a ciliary portion including many cilia inclined in a longitudinal direction of the tube, provided in an outer peripheral portion of the tube, and a vibration portion disposed on the tube for vibrating the ciliary portion so as to move the tube in the longitudinal direction; a vibration operation portion for operating a vibration control portion for controlling the vibration portion; and a power reception connector for receiving drive power for the vibration portion.

Also, an endoscope system in another embodiment of the present invention includes an endoscope apparatus having an insertion portion having an image pickup portion at a distal end portion, an endoscope operation portion for operating the insertion portion, disposed on a proximal end portion side of the insertion portion, a main body portion having a power supply portion disposed therein, and a power transmission connector for transmitting power from the power supply portion; and a guide tube apparatus having a guide tube having a tube having an inner diameter such that the insertion portion can be inserted, a ciliary portion including many cilia inclined in a longitudinal direction of the tube, provided in an outer peripheral portion of the tube, and a vibration portion disposed on the tube for vibrating the ciliary portion so as to move the tube in the longitudinal direction, a vibration operation portion attachable to and detachable from the endoscope operation portion for operating the vibration portion, and a power reception connector connectable to the power transmission connector.

Further, in a method for using an endoscope system in another embodiment of the present invention, the endoscope system includes an endoscope apparatus and a guide tube apparatus, the endoscope apparatus has an insertion portion having an image pickup portion at a distal end portion, an endoscope operation portion for operating the insertion portion, disposed on a proximal end portion side of the insertion portion, a main body portion having a power supply portion disposed therein, and a power transmission connector for transmitting power from the power supply portion, the guide tube apparatus has a guide tube having a tube having an inner diameter such that the insertion portion can be inserted, a ciliary portion including many cilia inclined in a longitudinal direction of the tube, provided in an outer peripheral portion of the tube, and a vibration portion disposed on the tube for vibrating the ciliary portion so as to move the tube in the longitudinal direction, the insertion portion of the endoscope apparatus is inserted into the tube of the guide tube apparatus, and the tube is moved in the longitudinal direction by driving the vibration portion to vibrate the ciliary portion.

DETAILED DESCRIPTION OF THE PREFERRED EMBODIMENTS

<First Embodiment>

An endoscope system 1 in a first embodiment, a guide tube 10 in the first embodiment, and a guide tube apparatus 20 in the first embodiment will be described below with reference to drawings. Hereinafter, an endoscope system, a guide tube, and a guide tube apparatus are referred to as an endoscope system and the like.

Figure 1:
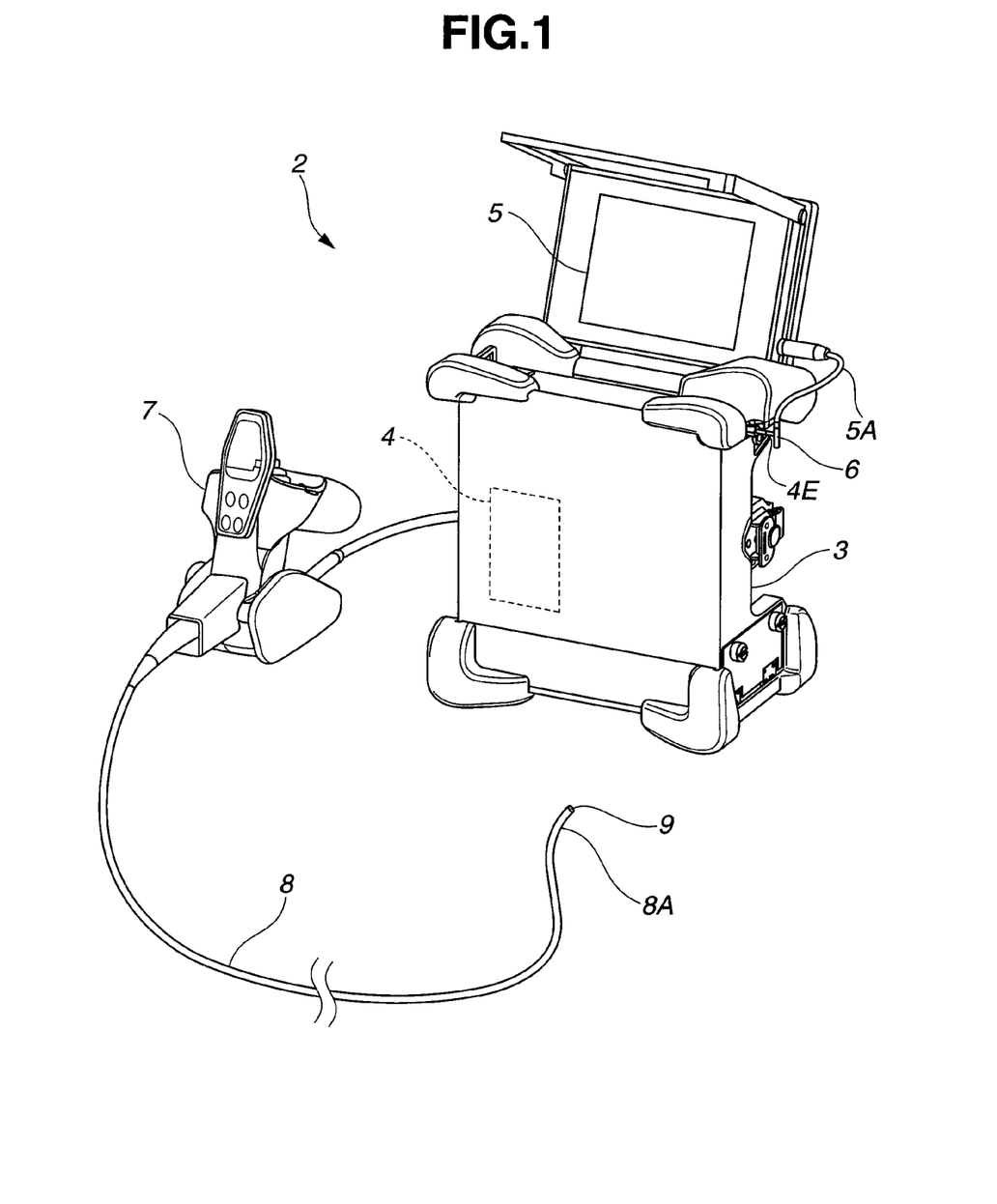
FIG. 1 is an appearance view showing an appearance of an endoscope apparatus used in combination with a guide tube apparatus in a first embodiment.

FIG. 1 shows an endoscope apparatus 2 used in combination with the guide tube apparatus 20 in the present embodiment. A basic configuration of the endoscope apparatus 2 is such that the endoscope apparatus 2 has a main body portion 3, an endoscope operation portion 7, and an elongated insertion portion 8. A CCD 9, which is an image pickup portion, is disposed at a distal end portion 8A of the insertion portion 8. A power supply portion 4 for supplying power, and a processing portion 3A (see FIG. 4) composed of various processing boards and the like not shown are contained in the main body portion 3. An LCD 5, which is a display portion for displaying an endoscopic image and the like, is disposed detachably from the main body portion 3, and the LCD 5 operates by receiving supply of power from the power supply portion 4 in the main body portion 3. Further, the endoscope apparatus 2 has a connector 6, which is a power transmission connector for supplying power not only to the LCD 5 but also to the guide tube apparatus 20 from the power supply portion 4. The connector 6 has a structure for branching a power transmission line 4E from the power supply portion 4. In other words, the endoscope apparatus 2 is such that a power transmission connector for supplying power to the LCD 5 of the endoscope apparatus is replaced by the connector 6 having the branch structure, and a power transmission line 5A to the LCD 5 is connected to the connector 6.

Figure 2:
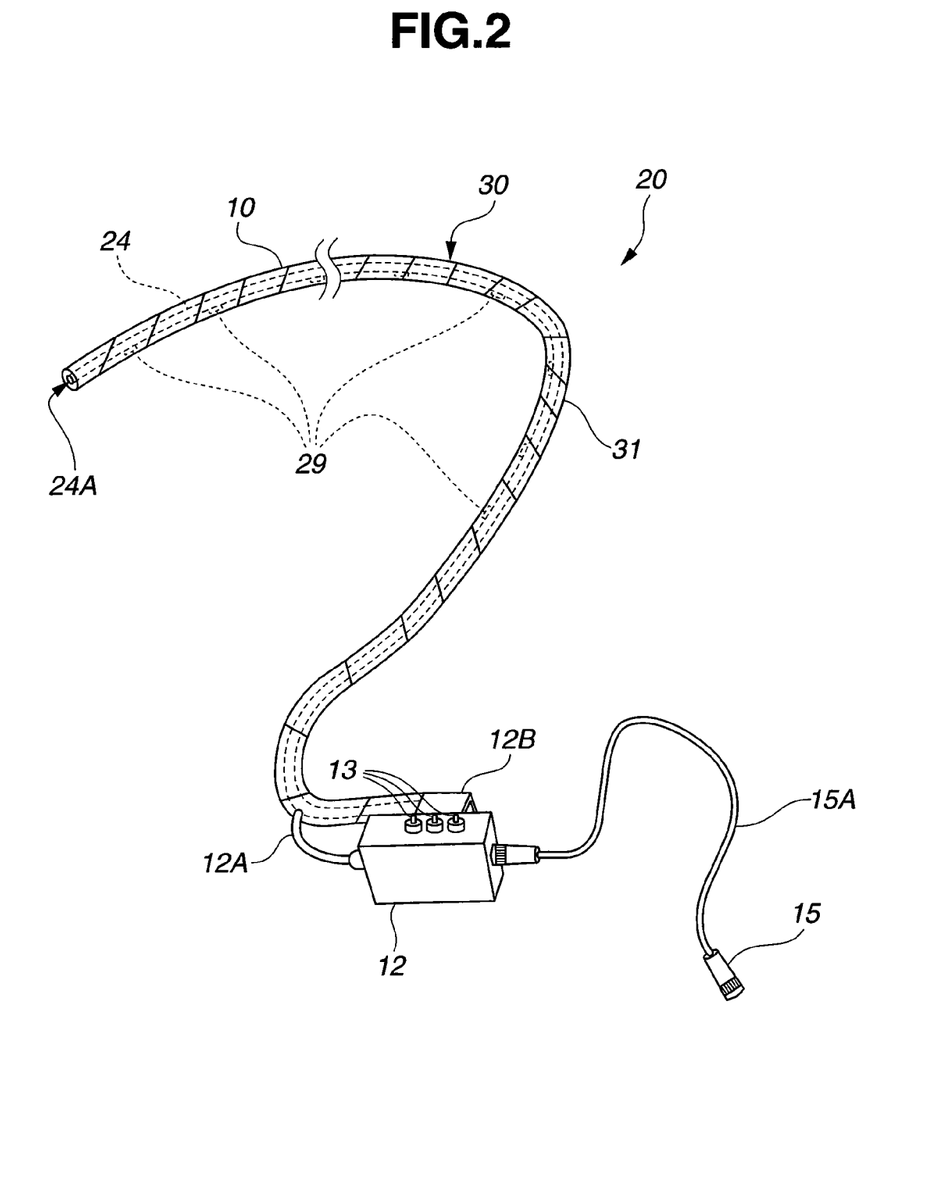
FIG. 2 is an appearance view showing an appearance of a guide tube apparatus in the first embodiment.

On the other hand, the guide tube apparatus 20 shown in FIG. 2 has the guide tube 10 and a vibration operation portion 12. The guide tube 10 has an elongated shape in which a tube 24 having an insertion hole 24A having an inner diameter such that the insertion portion 8 of the endoscope apparatus 2 can be inserted is a so-called core, and a ciliary portion 30 having many cilia 31 is provided in an outer peripheral portion of the tube 24.

The vibration operation portion 12 is connected via a power supply line 15A to a connector 15, which is a power reception connector for receiving power, and drives vibration motors 21 in vibration portions 29 connected via a signal line 12A, by operation of a switch portion 13. A fixing jig 12B for attaching to and detaching from the endoscope operation portion 7 is disposed in the vibration operation portion 12.

Figure 3:
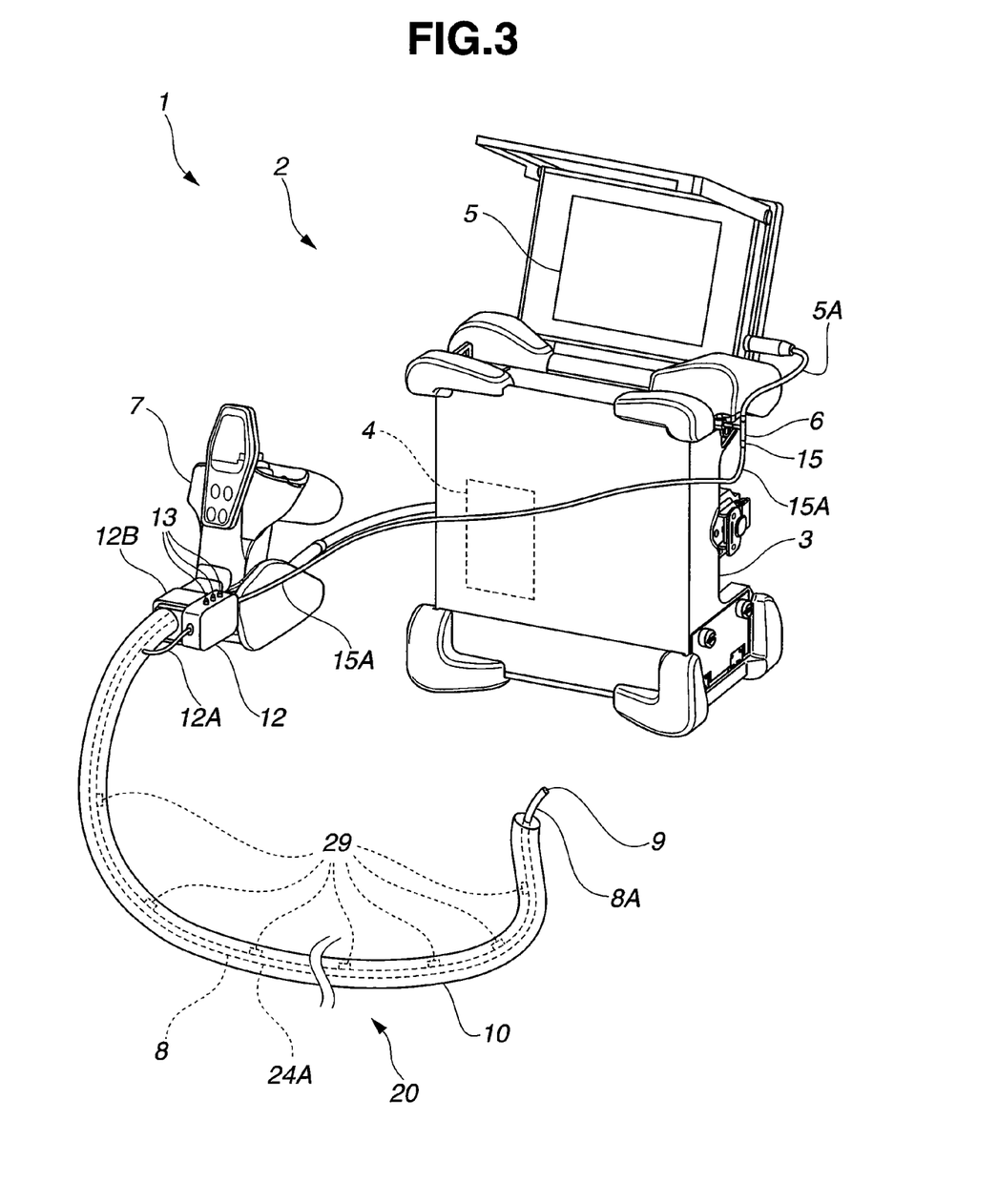
FIG. 3 is an appearance view showing an appearance of an endoscope system in the first embodiment.

As shown in FIG. 3, the endoscope system 1 is constituted by integrating the guide tube apparatus 20 and the endoscope apparatus 2. In other words, the insertion portion 8 of the endoscope apparatus 2 is inserted into the insertion hole 24A of the guide tube 10, the vibration operation portion 12 of the guide tube apparatus 20 is fixed to the endoscope operation portion 7 of the endoscope apparatus 2 by the fixing jig 12B, and the connector 15, which is the power reception connector of the guide tube apparatus 20, is connected to the connector 6, which is the power transmission connector of the endoscope apparatus 2. The power transmission connector may be disposed in the endoscope operation portion 7.

Figure 4:
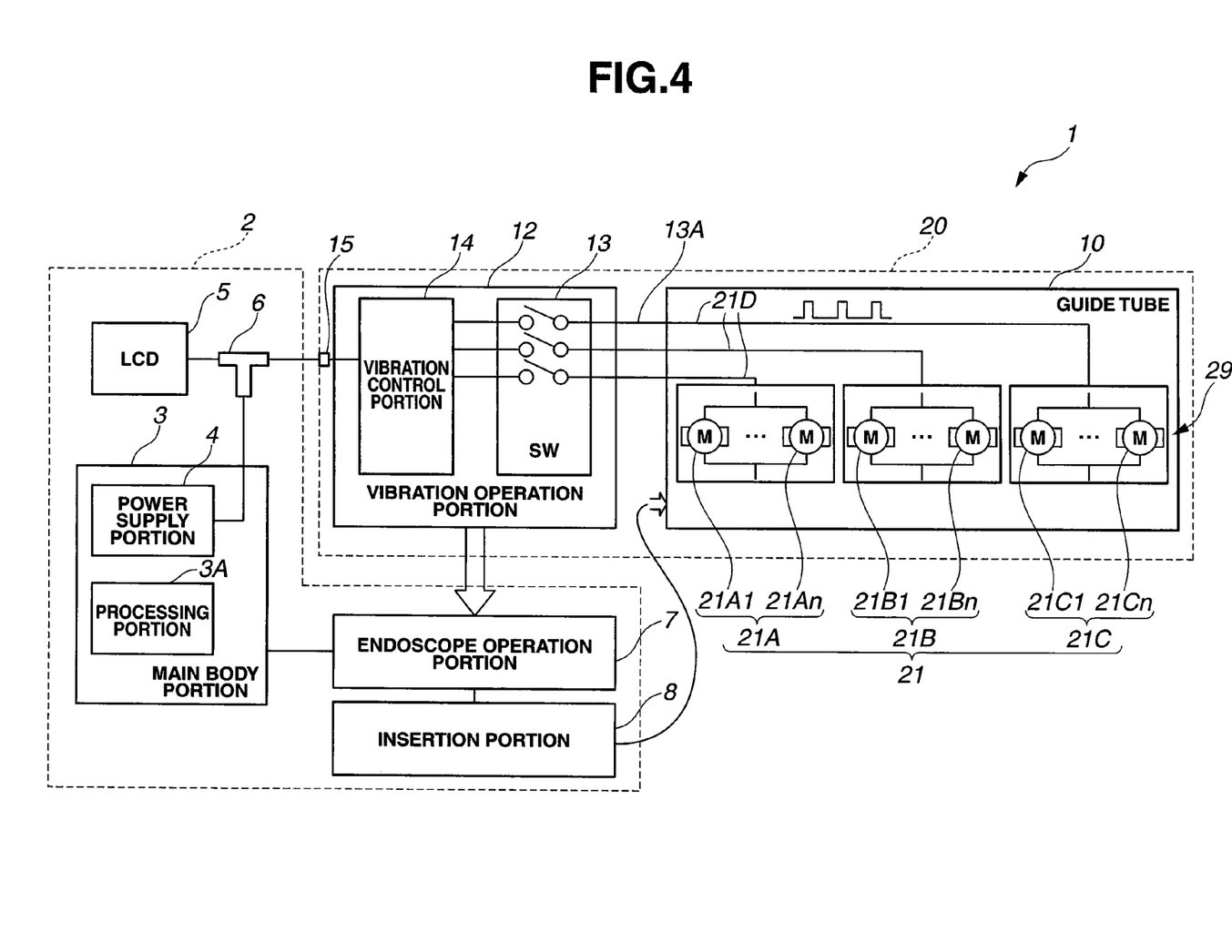
FIG. 4 is a configuration view showing a configuration of the endoscope system in the first embodiment.

Next, as shown in FIG. 4, the vibration operation portion 12 has a vibration control portion 14 for controlling vibration, and the switch portion 13 for selecting the vibration motors 21 that vibrate. The guide tube apparatus 20 can drive part of vibration motors 21 selected by the switch portion 13, among the plurality of vibration motors 21 disposed at intervals in a longitudinal direction of the tube 24. In other words, the vibration motors 21 of the guide tube 10 illustrated in FIG. 4 are broadly divided into a vibration motor group 21A on a proximal end portion side, a vibration motor group 21B in a central portion, and a vibration motor group 21C on a distal end portion side, and can be driven for each vibration motor group. Each vibration motor group includes n (n≥ an integer of 2) vibration motors, for example, 21A1 to 21An. Therefore, in the endoscope system 1 and the like, the user can selectively vibrate part of the guide tube 10.

The vibration motors 21 are not limited to the vibration motor groups (21A, 21B, and 21C). The single vibration motor 21 may be located in a plurality of places, and each vibration motor may be independently controllable. Also, a number of the vibration motors 21 in the vibration motor groups (21A, 21B, and 21C) may be different.

Next, a structure of the vibration portion 29 of the guide tube 10 in the present embodiment will be described using FIG. 5, FIG. 6, and FIG. 7.

Figure 5:
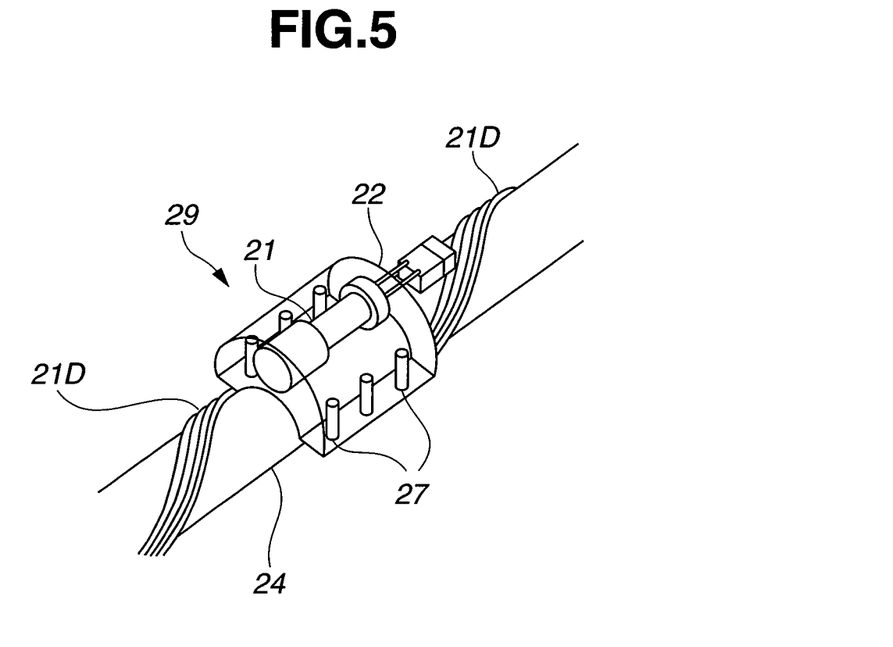
FIG. 5 is a transparent perspective view for explaining a structure of a vibration portion of the guide tube apparatus in the first embodiment.
Figure 6:
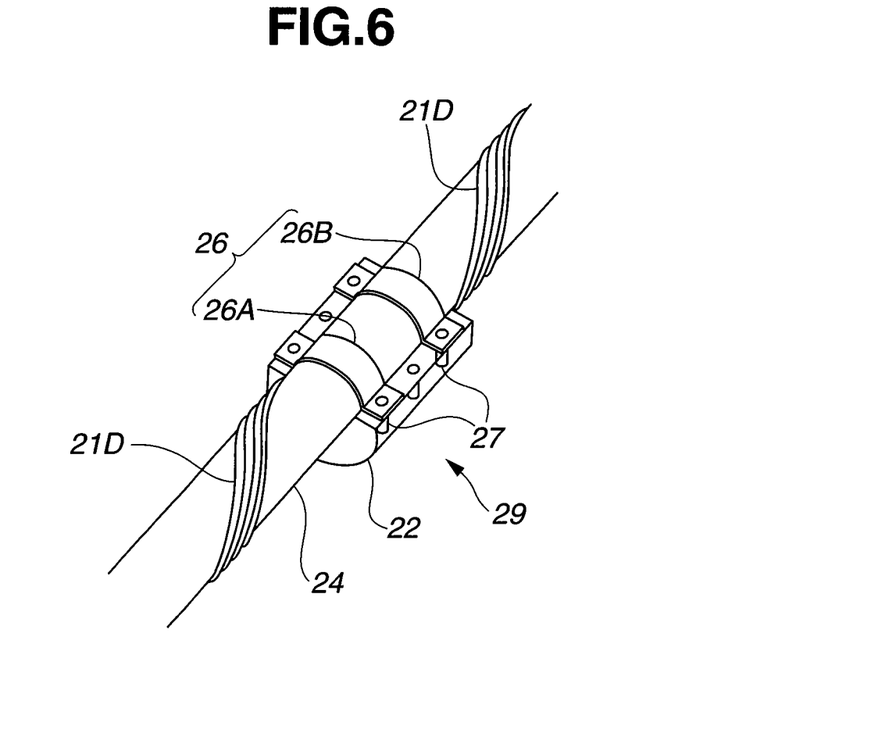
FIG. 6 is a perspective view for explaining the structure of the vibration portion of the guide tube apparatus in the first embodiment.
Figure 7:
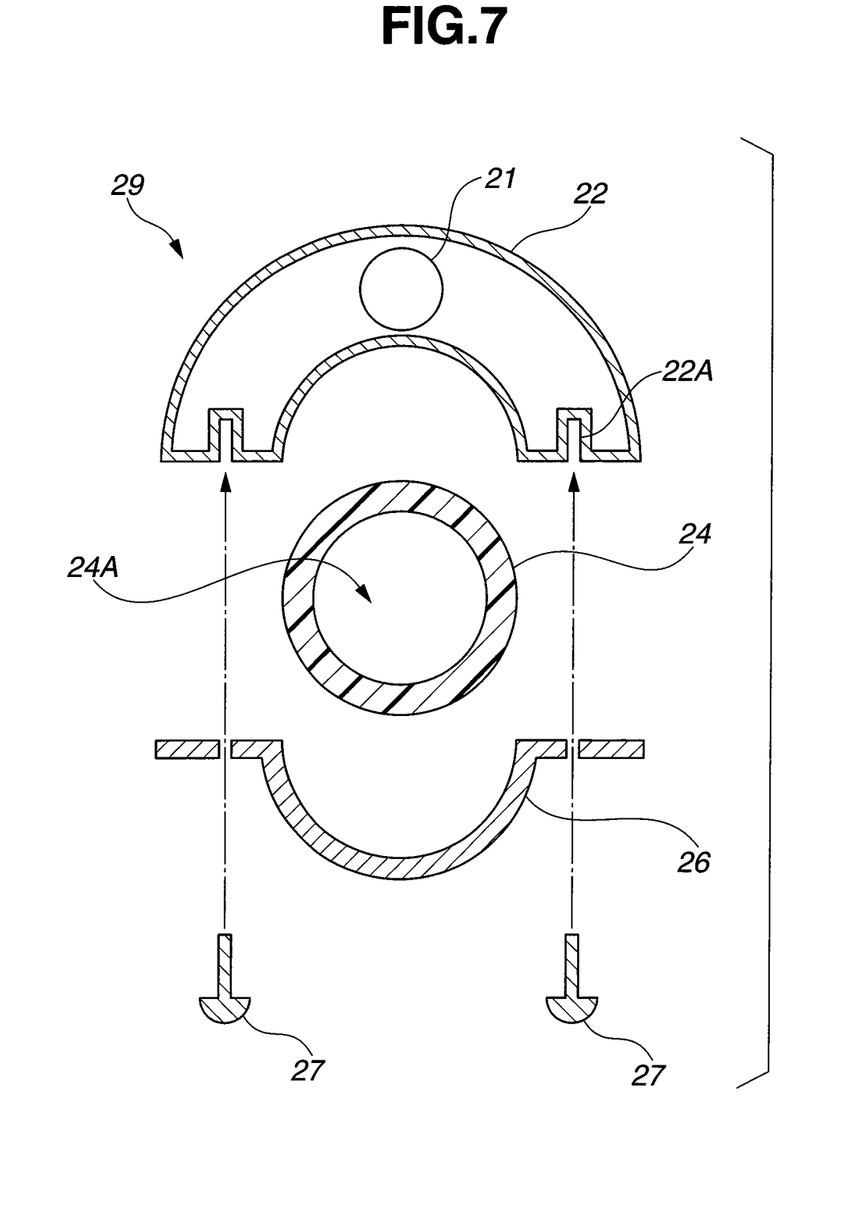
FIG. 7 is an exploded cross-sectional schematic view for explaining the structure of the vibration portion of the guide tube apparatus in the first embodiment.

As shown in FIG. 5 and FIG. 6, the vibration portion 29 has the vibration motor 21, and a motor case 22, which is a semicylindrical metal case housing the vibration motor 21 and having a shape in which an inner peripheral portion is in close contact with the tube 24, and the vibration portion 29 is mechanically fixed to the tube 24. In other words, the motor case 22 is fixed to the tube 24 by locating a metal fixing jig 26, in which part of a cross section is semicircular, in close contact with the tube 24 on a side opposite to the motor case 22 and using a screw 27, as shown in FIG. 7.

As shown in FIG. 5 and FIG. 6, a power line 21D for supplying power to the vibration motor 21 is located, spirally wound around the tube 24. Therefore, in the endoscope system 1 and the like, the power line 21D is not subjected to particularly strong deformation when the tube 24 is bent in a specific direction, and thus, the power line 21D is not easily broken.

In the vibration motor 21, a weight is disposed at a position offset from a center of a rotation axis of a shaft of the motor that rotates by an electromagnetic force by combining a permanent magnet and an electromagnet, and when the shaft rotates, the vibration motor 21 vibrates by a centrifugal force of the weight. The vibration portion 29 in the present embodiment has the above configuration, and therefore, the vibration portion 29 in the present embodiment can efficiently transmit vibration, compared with a vibration portion fixed to the tube 24 using resin.

Figure 8:
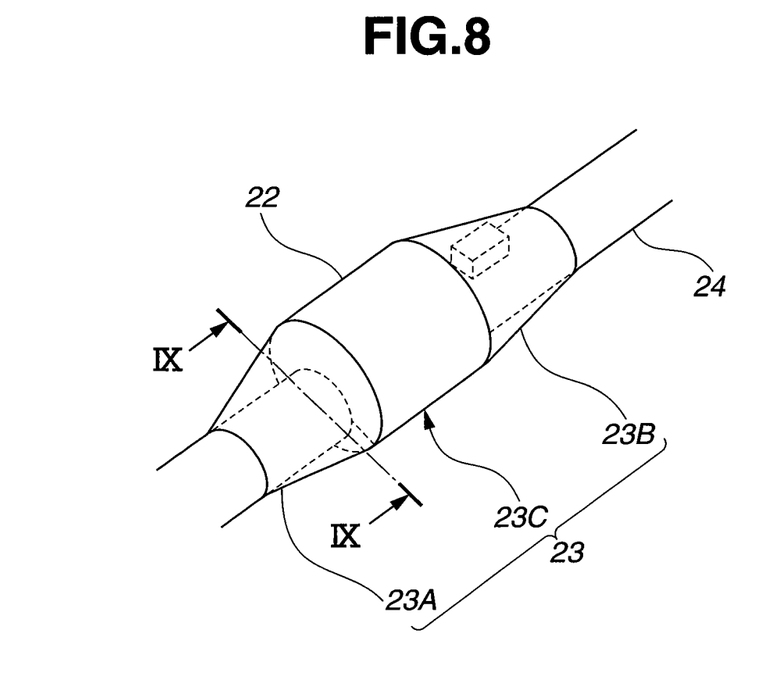
FIG. 8 is a perspective view for explaining a step reducing portion in the first embodiment.

Next, a step reducing portion 23 of the guide tube 10 will be described using FIG. 8 and FIG. 9.

As described in FIG. 5 and FIG. 6, the guide tube 10 in the present embodiment has a structure in which the motor case 22 protrudes from the outer peripheral portion of the tube 24. But, as shown in FIG. 8 and FIG. 9, the guide tube 10 has the step reducing portion 23 for reducing a step in a circumferential direction between the motor case 22 and the outer peripheral portion of the tube 24. In other words, the step reducing portion 23 has a function of making a size that a ciliary tape 30A (see FIG. 10) is wound around a portion in proximity to the motor case 22 a size of the motor case 22. The step reducing portion 23 includes a front portion 23A, a back portion 23B, and a middle portion 23C, and is designed to have inclination from a size of the tube 24 to the size of the motor case 22 to transit gradually. Therefore, in the endoscope system 1 and the like, the ciliary tape 30A is easily wound around the tube 24.

Figure 9:
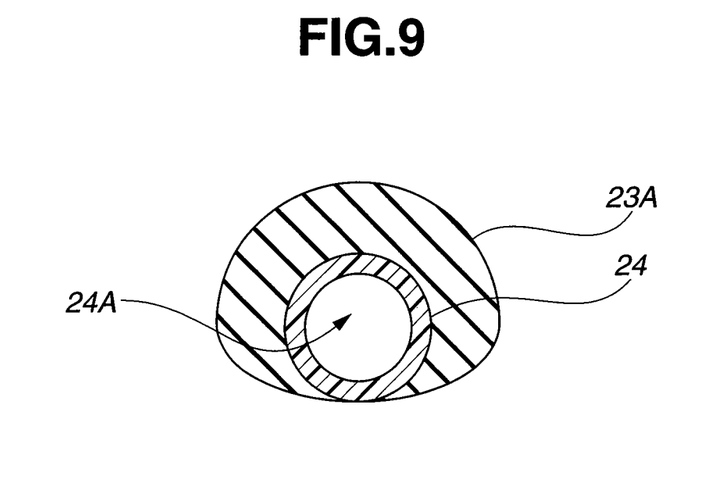
FIG. 9 is a cross-sectional schematic view of a guide tube in FIG. 8 taken on line IX-IX.

Here, the step reducing portion 23 shown in FIG. 9 is formed of a resin having flexibility and can be opened toward both sides in a lower portion, and therefore, the step reducing portion 23 is attachable to and detachable from the tube 24. The step reducing portion 23 is not limited to those having an inclination structure. The step reducing portion 23 may have, for example, a structure in which a spiral step suited to a width of the ciliary tape 30A is formed, and may be made of metal, or may be rubber, as long as the step reducing portion 23 has a structure in which the ciliary tape 30A is easily wound.

Next, the ciliary tape 30A of the guide tube 10 will be described using FIG. 10 and FIG. 11. Cilia of the ciliary tape 30A are not shown in FIG. 10, but are shown in FIG. 11.

Figure 10:
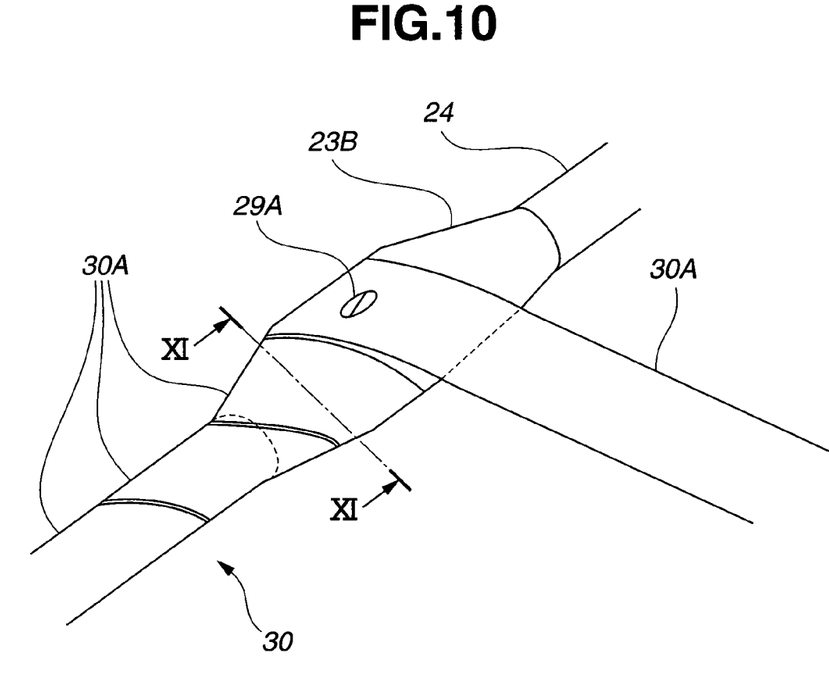
FIG. 10 is a perspective view for explaining a way of winding a ciliary tape in the step reducing portion in the first embodiment.
Figure 11:
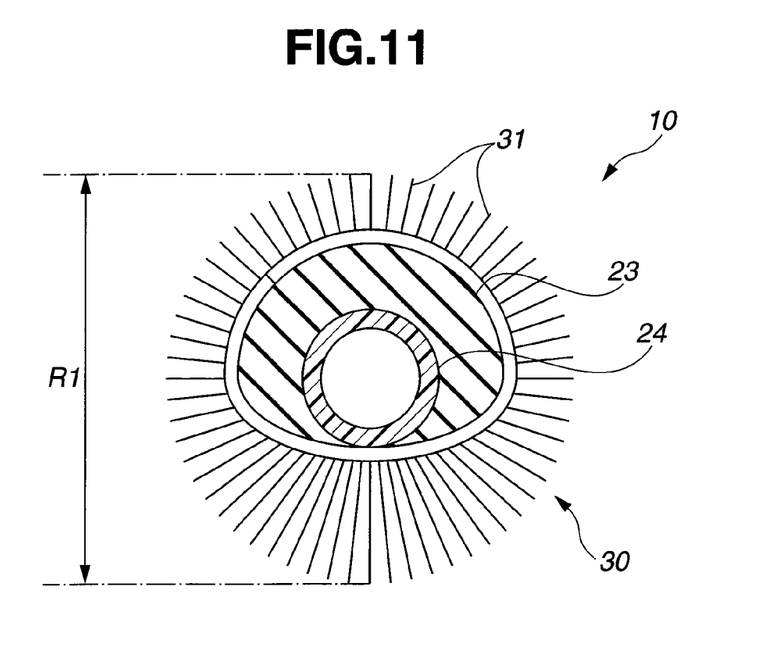
FIG. 11 is a cross-sectional schematic view taken on line XI-XI in FIG. 10.

As shown in FIG. 10, the ciliary portion 30 is formed by spirally winding the ciliary tape 30A around the tube 24. The cilia 31 of the ciliary tape 30A, for example, have a diameter of 0.01 mm and a cilium length of 7 to 10 mm, are made of nylon, and are formed with a density of about 2500 cilia/cm$^2$. The ciliary tape 30A having the cilia 31 inclined at a desired angle, for example, 60 degrees, can be obtained by subjecting a ciliary tape having the upright cilia 31, with the cilia inclined and deformed, to a heating process at a temperature equal to or higher than a thermoplastic deformation temperature of a material of the cilia 31 and a temperature decreasing process. The cilia 31 may be an inorganic substance, such as a metal wire and a metal plate, as long as the cilia 31 are columnar structures.

The ciliary tape 30A having the inclined cilia 31 is wound around the tube 24, thereby, the ciliary portion 30 having the cilia 31 inclined in the longitudinal direction of the tube 24 is formed in the outer peripheral portion of the tube 24. Here, the cilia 31 are preferably inclined in a proximal end portion direction to self-propel the guide tube 10 in a distal end direction. The cilia 31 of the ciliary tape 30A have inclination at a spiral angle from the longitudinal direction of the tube 24 when the ciliary tape 30A is spirally wound around the tube 24. In other words, an inclination direction of the cilia 31 need not perfectly match the longitudinal direction of the tube 24 as long as it has a longitudinal direction component. For example, the cilia 31 may be inclined at about 45 degrees from the longitudinal direction of the tube 24.

The ciliary tape 30A of the guide tube 10 is fixed to the tube 24 in the vibration portion 29, using a screw 29A, which is a mechanical fixing member. Therefore, in the endoscope system 1 and the like, the ciliary tape 30A is not easily detached from the tube 24 even if the guide tube 10 is subjected to stress, and the ciliary tape 30A is easily replaced when the ciliary tape 30A is dirty, and the like, compared with a case where the ciliary tape 30A is fixed to the tube 24 by an adhesive tape.

The ciliary tape 30A is wound after the vibration portions 29 and the step reducing portions 23 are disposed in the outer peripheral portion of the tube 24. Therefore, in a place on the tube 24 where the vibration portion 29 or the step reducing portion 23 is provided, the ciliary portion 30 is disposed on an outer surface of the vibration portion 29 or the step reducing portion 23, and the ciliary portion 30 is not disposed on the tube 24 in contact with the vibration portion 29 or the step reducing portion 23.

As shown in FIG. 11, in the guide tube 10, a length of the cilia 31 of the ciliary tape 30A wound around the motor case 22 and the portion in proximity to the motor case 22 is shorter than a length of the cilia 31 in other portions. In other words, a maximum outer diameter R1 of the guide tube 10 in the motor case 22 and the portion in proximity to the motor case 22 can be formed to be the same as the maximum outer diameter R1 of the guide tube 10 in other portions.

The maximum outer diameter R1 is an outer diameter of the guide tube 10 including distal end portions of the cilia 31, as shown in FIG. 11. In the endoscope system 1 and the like, self-propelling properties, for example, traveling speed, can be faster, when an area where the distal end portions of the cilia 31 are in contact with surrounding ground and the like is increased in the guide tube 10.

Figure 12A:
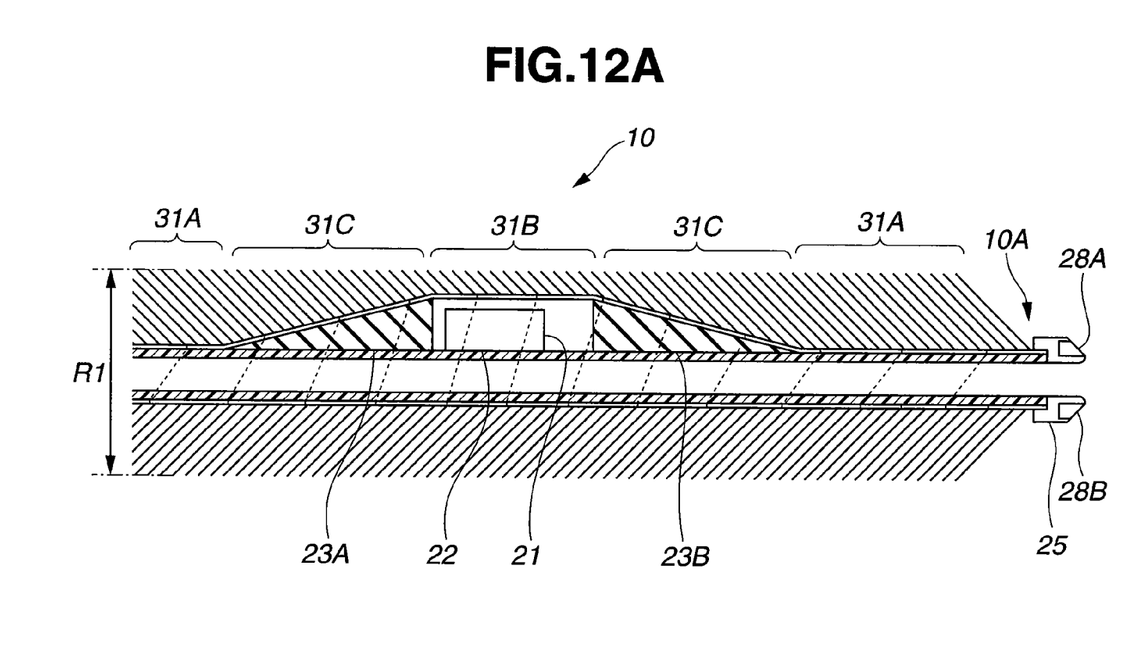
FIG. 12A is a longitudinal cross-sectional view for explaining a structure of a vicinity of a distal end portion of the guide tube in the first embodiment.
Figure 12B:
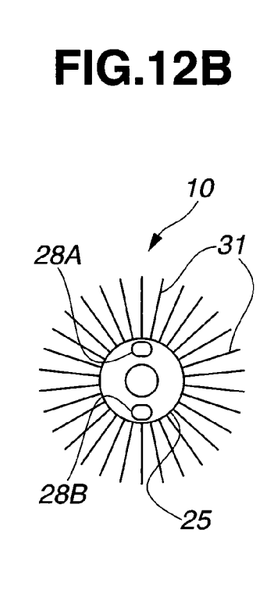
FIG. 12B is an appearance view showing an appearance when observed from a distal end portion direction for explaining the structure of the vicinity of the distal end portion of the guide tube in the first embodiment.

Next, as shown in FIG. 12(A), a distal end portion fixture 25 having a microphone 28A and a speaker 28B is disposed at a distal end portion of the guide tube 10.

As already described, in the guide tube 10, a length of cilia 31B in a motor case 22 portion and cilia 31C in the portion in proximity to the motor case 22 is shorter than a length of cilia 31A in other portions. That is, the maximum outer diameter R1 of the guide tube 10 in the motor case 22 portion and the portion in proximity to the motor case 22 is formed to be the same as the maximum outer diameter R1 of the guide tube 10 in other portions.

Next, a mode in which the endoscope system 1 in the present embodiment is used will be described by an example in which rubble is searched for victims at a disaster site. As shown in FIG. 3, the user can handle the endoscope apparatus 2 and the guide tube apparatus 20 as one endoscope system 1 by integrating the endoscope apparatus 2 and the guide tube apparatus 20, and therefore, the endoscope system 1 has excellent portability. Also, in the endoscope system 1 and the like, a power supply need not be separately prepared for the guide tube apparatus.

The user inserts the guide tube 10 into a gap in rubble in a direction of a position where a victim may exist. Then, the user operates the switch portion 13 of the vibration operation portion 12 to vibrate the vibration motor group 21C on the distal end portion side. Then, distal ends of the cilia 31 of the ciliary portion 30 vibrated by vibration motors 21C1 to 21Cn perform elliptic motion by repulsion generated by friction between the distal ends of the cilia 31 and surrounding rubble, thereby, propulsion in a longitudinal direction, that is, a distal end portion direction, is generated. Therefore, the guide tube 10 into which the insertion portion 8 is inserted moves by itself through the gap in the rubble into a deep portion in the longitudinal direction. In other words, the vibration portion 29 vibrates the ciliary portion 30 so as to move the tube 24 in the longitudinal direction.

The user can check, using LCD 5, an endoscopic image photographed by the CCD 9 disposed at the distal end portion 8A of the insertion portion 8 of the endoscope apparatus 2 also during self-propelling of the guide tube 10, and bends the insertion portion 8 as required. Even if the user holds a proximal end portion side of the long guide tube 10 with his (her) hand, the proximal end portion side does not vibrate, and therefore, the endoscope system 1 and the like have good operability.

The guide tube 10 is self-propelled in the rubble, and at a stage in which a central portion of the guide tube 10 enters the rubble, the user operates the switch portion 13 to start vibration of the vibration motor group 21B in the central portion. In the guide tube apparatus 20, the vibration operation portion 12 is integrated with the endoscope operation portion 7 by the fixing jig 12B, and therefore, the user can simultaneously perform endoscope operation and vibration operation.

The guide tube 10 is further self-propelled in the rubble, and at a stage in which the proximal end portion side of the guide tube 10 enters the rubble, the user operates the switch portion 13 to start vibration of the vibration motor group 21A on the proximal end portion side. Further, the user may drive part of the vibration motor groups according to conditions around the guide tube 10. In the guide tube apparatus 20, necessary vibration motors can be driven, and therefore, the guide tube apparatus 20 can be used for a long time even if a battery is used as a power supply.

The user may self-propel the guide tube 10, with a distal end portion of the insertion portion 8 not inserted into the tube 24 to a distal end portion 10A of the guide tube 10, according to conditions of the rubble, and the like. In this case, the guide tube 10 in a portion where the insertion portion 8 is not inserted has excellent flexibility and is easily bent, and therefore, the guide tube 10 easily enters the deep portion along a path in which the guide tube 10 can advance in a curved space. In addition, the guide tube 10 in a portion where the insertion portion 8 is inserted has rigidity to some extent, and therefore, handling is easy when the user operates the guide tube 10, holding the guide tube 10 with his (her) hand.

In the guide tube apparatus 20, when a victim can be recognized in the rubble with an endoscopic image, the user can converse with a victim using the microphone 28A or the speaker 28B at the distal end portion 10A. Further, in the guide tube apparatus 20, the insertion portion 8 of the endoscope apparatus 2 can be pulled out from the tube 24, and a supply tube for supplying air, water, or the like to the victim can be inserted into the tube 24.

In other words, since the endoscope system 1 has the guide tube 10, it is not only easy to insert the distal end portion 8A of the endoscope apparatus 2 to a target position, but also it is possible to contribute to aid of the victim, and the like, by inserting a tool suited to conditions of a site into the tube 24, instead of the insertion portion 8, with the distal end portion 10A remaining at the target position.

In a self-propelled endoscope in which a ciliary portion is disposed on an insertion portion itself, an outer diameter of the insertion portion is large, and the insertion portion may not be inserted into a narrow gap. But, in the endoscope system 1, it is also possible to use the endoscope apparatus 2 alone according to conditions, though the user needs to insert the insertion portion by hand.

<Second Embodiment>

An endoscope system and the like in a second embodiment of the present invention will be described below. An endoscope system 1B and the like in the present embodiment are similar to the endoscope system 1 and the like in the first embodiment, and therefore, like components are referred to by like numerals, and description is omitted.

Figure 13:
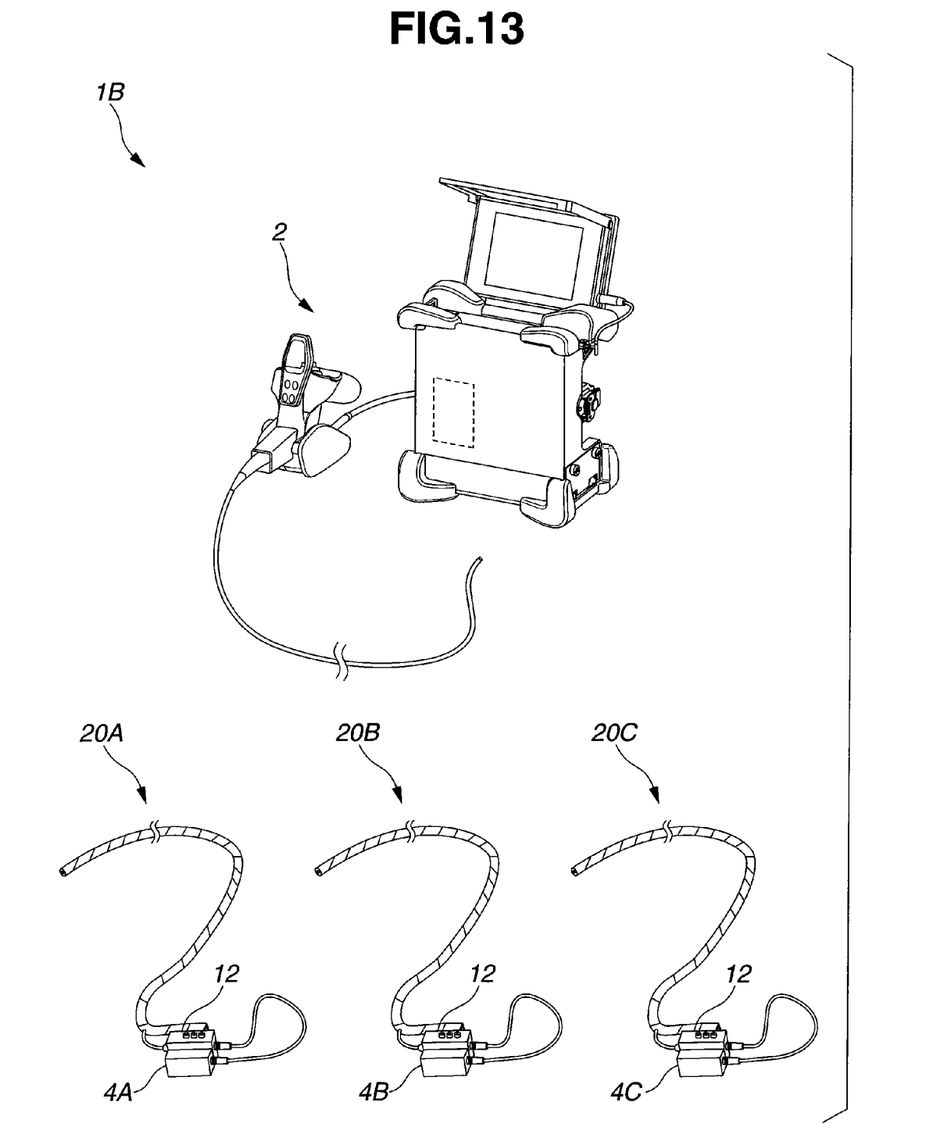
FIG. 13 is an appearance view showing a configuration of an endoscope system in a second embodiment.

As shown in FIG. 13, the endoscope system 1B in the present embodiment has one endoscope apparatus 2 and a plurality of guide tube apparatuses 20A to 20C. The guide tube apparatuses 20A to 20C have power supply portions 4A to 4C respectively. In FIG. 13, an example in which the power supply portions 4A to 4C are integrated with vibration operation portions 12 is shown, but the power supply portions 4A to 4C may be housed in interiors of respective vibration operation portions 12. Further, specifications of power supplied by the power supply portions 4A to 4C are preferably the same as specifications of power supplied by a power supply portion 4 of the endoscope apparatus 2 to an LCD 5 and the like because the guide tube apparatuses 20A to 20C can not only receive supply of power from the power supply portion 4, but also supply power to the LCD 5 and the like of the endoscope apparatus 2, on the contrary, according to conditions.

Each of the guide tube apparatuses 20A to 20C can also be used alone. Therefore, the user can use the guide tube apparatuses 20A to 20C in different places respectively. That is, the user can insert respective guide tubes at different target positions. Although the user requires time to operate the guide tube to insert the guide tube to a target position, the user can insert an insertion portion 8 of the endoscope apparatus 2 into a tube 24 of the guide tube apparatus, in which insertion at a target position is completed, among the plurality of guide tube apparatuses 20A to 20C, to check an endoscopic image at the target position.

In other words, since the endoscope apparatus 2 is expensive, there is an economical problem in preparing many endoscope apparatuses 2. But, the endoscope system 1B has one endoscope apparatus 2 and the plurality of relatively inexpensive guide tube apparatuses 20A to 20C, and therefore, work can be efficiently performed.

Particularly, the guide tube apparatuses 20A to 20C are self-propelled guide tube apparatuses, and therefore, the user need not operate the guide tube apparatuses 20A to 20C all the time. The user can operate each guide tube 10 until start of self-propelling, and after start of self-propelling, the user can leave the guide tube 10 and perform self-propelling starting operation of another guide tube apparatus.

Of course, a plurality of users may operate respective guide tube apparatuses 20A to 20C, and the users may insert the insertion portion 8 of the endoscope apparatus 2 into any guide tube apparatus, in which operation of insertion at a target position is completed, to check an endoscopic image at the target position. Further, the insertion portion 8 of the endoscope apparatus 2 may be inserted into any of the plurality of guide tube apparatuses 20A to 20C from time of start of self-propelling. The endoscope system 1B may be an endoscope system including a plurality of the endoscope apparatuses 2 and the guide tube apparatuses 20 whose number is larger than the number of the endoscope apparatuses 2.

When the endoscope system 1B is used for search for victims in rubble, and the like, a vibration control portion 14 performs control, based on information from a microphone at a distal end portion 10A of the guide tube 10, for example, to stop self-propelling when a human voice or the like is detected, thereby, workability can be further improved.

In the above, an example in which particularly the vibration motor 21 for generating vibration by an electromagnetic force is used for the vibration portion 29 has been described, but a vibration portion using a piezoelectric element, a vibration portion using an ultrasound transducer, a vibration portion using a magnetostrictive element, or the like can be used. When a vibration portion having an elongated structure is used, part of the vibration portion can be preferably vibrated.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A guide tube comprising:
   a tube;
   a ciliary portion including many cilia inclined in a longitudinal direction of the tube, provided in an outer peripheral portion of the tube; and
   a vibration portion provided on the tube for vibrating the ciliary portion so as to move the tube in the longitudinal direction,
   wherein the ciliary portion is fixed to the tube in the vibration portion,
   wherein the ciliary portion is fixed to the tube by a fixing member,
   wherein the ciliary portion is constituted by winding a ciliary tape having cilia on one surface around the tube, comprising
   a plurality of the vibration portions,
   wherein part of the plurality of the vibration portions can be selectively driven,
   wherein the vibration portion has a vibration motor, and a case housing the vibration motor and having a shape in which an inner peripheral portion is in close contact with the tube, and a step reducing portion for reducing a step in a longitudinal direction between the case and a surface of the tube.

2. The guide tube according to claim 1, wherein a length of the cilia of the ciliary portion provided in an outer peripheral portion of the case is shorter than a length of the cilia in other portions.

3. A guide tube comprising:
a tube;
a ciliary portion including many cilia inclined in a longitudinal direction of the tube, provided in an outer peripheral portion of the tube; and
a vibration portion provided on the tube for vibrating the ciliary portion so as to move the tube in the longitudinal direction,
wherein the ciliary portion is fixed to the tube in the vibration portion,
wherein the ciliary portion is fixed to the tube by a fixing member,
wherein the ciliary portion is constituted by winding a ciliary tape having cilia on one surface around the tube, comprising
a plurality of the vibration portions,
wherein part of the plurality of the vibration portions can be selectively driven,
wherein the vibration portion has a vibration motor, and a case housing the vibration motor and having a shape in which an inner peripheral portion is in close contact with the tube, and
at least any one of a microphone or a speaker at a distal end portion.

4. A guide tube comprising:
a tube;
a ciliary portion including many cilia inclined in a longitudinal direction of the tube, provided in an outer peripheral portion of the tube; and
a vibration portion provided on the tube for vibrating the ciliary portion so as to move the tube in the longitudinal direction,
wherein the ciliary portion is fixed to the tube in the vibration portion,
wherein the ciliary portion is fixed to the tube by a fixing member,
wherein the ciliary portion is constituted by winding a ciliary tape having cilia on one surface around the tube, comprising
a plurality of the vibration portions,
wherein part of the plurality of the vibration portions can be selectively driven,
wherein the vibration portion has a vibration motor, and a case housing the vibration motor and having a shape in which an inner peripheral portion is in close contact with the tube, and
wherein the tube has an inner diameter such that an insertion portion of an endoscope apparatus having an image pickup portion disposed at a distal end portion can be inserted.

5. A method for using an endoscope system,
wherein the endoscope system comprises an endoscope apparatus and a guide tube apparatus,
the endoscope apparatus has an insertion portion having an image pickup portion at a distal end portion, an endoscope operation portion for operating the insertion portion, disposed on a proximal end portion side of the insertion portion, a main body portion having a power supply portion disposed therein, and a power transmission connector for transmitting power from the power supply portion to the guide tube apparatus,
the guide tube apparatus has a guide tube having a tube having an inner diameter such that the insertion portion can be inserted, a ciliary portion including many cilia inclined in a longitudinal direction of the tube, provided in an outer peripheral portion of the tube, and a vibration portion disposed on the tube for vibrating the ciliary portion so as to move the tube in the longitudinal direction, and
the tube is moved in the longitudinal direction by driving the vibration portion to vibrate the ciliary portion
wherein the endoscope system comprises at least one of the endoscope apparatus and a plurality of the guide tube apparatuses, and
the tube is moved in the longitudinal direction by driving the vibration portion of the non-inserted guide tube apparatus, in which the insertion portion is not inserted into the tube, to vibrate the ciliary portion.

6. The method for using an endoscope system according to claim 5, wherein the insertion portion is inserted into the tube when a distal end portion of the non-inserted guide tube apparatus advances to a predetermined position.

7. The method for using an endoscope system according to claim 6, wherein the guide tube apparatus has a microphone at the distal end portion, and the distal end portion of the guide tube apparatus advancing to the predetermined position is sensed, based on information from the microphone.

8. The method for using an endoscope system according to claim 6, wherein a supply tube for supplying air or water is inserted into the tube when a distal end portion of the guide tube apparatus advances to a predetermined position.

* * * * *